United States Patent
Horiuchi et al.

(10) Patent No.: US 11,276,826 B2
(45) Date of Patent: Mar. 15, 2022

(54) TRIPHENYLENO-BENZOHURAN COMPOUND AND ORGANIC LIGHT EMITTING ELEMENT INCLUDING THE SAME

(75) Inventors: Takayuki Horiuchi, Tokyo (JP); Jun Kamatani, Tokyo (JP); Kenichi Ikari, Abiko (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 950 days.

(21) Appl. No.: 14/128,786

(22) PCT Filed: May 30, 2012

(86) PCT No.: PCT/JP2012/064493
§ 371 (c)(1),
(2), (4) Date: Mar. 31, 2014

(87) PCT Pub. No.: WO2013/001997
PCT Pub. Date: Jan. 3, 2013

(65) Prior Publication Data
US 2014/0197392 A1 Jul. 17, 2014

(30) Foreign Application Priority Data

Jun. 28, 2011 (JP) .............................. JP2011-143203

(51) Int. Cl.
| | | |
|---|---|---|
| H01L 51/54 | (2006.01) | |
| H01L 51/00 | (2006.01) | |
| C07D 409/10 | (2006.01) | |
| C07D 307/91 | (2006.01) | |
| C09K 11/06 | (2006.01) | |
| H01L 51/50 | (2006.01) | |
| H01L 27/32 | (2006.01) | |

(52) U.S. Cl.
CPC ........ *H01L 51/0073* (2013.01); *C07D 307/91* (2013.01); *C07D 409/10* (2013.01); *C09K 11/06* (2013.01); *H01L 51/0074* (2013.01); *C09K 2211/1007* (2013.01); *C09K 2211/1011* (2013.01); *C09K 2211/1088* (2013.01); *C09K 2211/1092* (2013.01); *H01L 27/3244* (2013.01); *H01L 51/006* (2013.01); *H01L 51/0067* (2013.01); *H01L 51/0085* (2013.01); *H01L 51/5012* (2013.01); *H01L 51/5016* (2013.01)

(58) Field of Classification Search
CPC ............ C09K 11/06; C09K 2211/1007; C09K 2211/1011; C09K 2211/1088; C09K 2211/1092; C09K 2211/1018; C09K 2211/105; H01L 51/006; H01L 51/0067; H01L 51/0071; H01L 51/0073; H01L 51/0074; H01L 51/0085; H01L 51/50; H01L 51/5012; H01L 51/5016; H01L 27/3244; C07D 307/78; C07D 307/87; C07D 307/91; C07D 333/52; C07D 333/72; C07D 333/76; C07D 409/02; C07D 409/10; C07D 405/02; C07D 405/10
USPC .... 549/41, 43, 456, 460; 428/690, 691, 917; 427/58, 66; 313/500–512; 257/40, 257/88–104, E51.001–E51.052; 252/301.16–301.35
See application file for complete search history.

(56) References Cited

U.S. PATENT DOCUMENTS

| | | | | |
|---|---|---|---|---|
| 2003/0067424 A1* | 4/2003 | Akimoto | .............. | G09G 3/3258 345/55 |
| 2006/0088728 A1* | 4/2006 | Kwong | ................ | C07D 209/82 428/690 |
| 2006/0227081 A1* | 10/2006 | Joo | ....................... | G09G 3/3233 345/76 |
| 2007/0141387 A1* | 6/2007 | Nakano | .................. | C09K 11/06 428/690 |

(Continued)

FOREIGN PATENT DOCUMENTS

| | | | |
|---|---|---|---|
| JP | 2008060379 A | * | 3/2008 |
| JP | 2009-123738 A | | 6/2009 |

(Continued)

OTHER PUBLICATIONS

Tavasli et al., "Colour tuning from green to red by substituent effects in phosphorescent tris-cyclometalated iridium(III) complexes of carbazole-based ligands: synthetic, photophysical, computational and high efficiency OLED studies", Journal of Materials Chemistry, (2012), vol. 22, pp. 6419-6428. (Year: 2012).*

(Continued)

*Primary Examiner* — Dylan C Kershner
(74) *Attorney, Agent, or Firm* — Canon U.S.A., Inc., IP Division

(57) ABSTRACT

An organic light emitting element which realizes a high efficiency and long-life light emission is provided. An organic compound represented by the general formula [1] described in Claim 1 is provided. In the general formula [1], $R_1$ to $R_3$ are each independently selected from a hydrogen atom, a substituted or unsubstituted aryl group, and a substituted or unsubstituted heterocyclic group. However, at least one of $R_1$ to $R_3$ represents the aryl group or the heterocyclic group. The aryl group represents a phenyl group, a naphthyl group, a phenanthrenyl group, a fluorenyl group, a triphenylenyl group, or a chrysenyl group. The heterocyclic group represents a dibenzofuranyl group or a dibenzothienyl group.

21 Claims, 1 Drawing Sheet

(56) References Cited

U.S. PATENT DOCUMENTS

| | | | |
|---|---|---|---|
| 2009/0230852 A1* | 9/2009 | Lee | C07C 13/567 313/504 |
| 2010/0237334 A1* | 9/2010 | Ma | C07D 307/91 257/40 |
| 2010/0301313 A1* | 12/2010 | Ito | C07D 209/86 257/40 |
| 2011/0266526 A1* | 11/2011 | Ma | C09K 11/06 257/40 |
| 2011/0315965 A1* | 12/2011 | Takashima | C07D 307/91 257/40 |

FOREIGN PATENT DOCUMENTS

| | | | | |
|---|---|---|---|---|
| JP | 2009-292807 A | | 12/2009 | |
| JP | WO 2010074087 A1 | * | 7/2010 | ............ C07D 307/91 |
| JP | 2011082238 A | * | 4/2011 | |
| WO | 2009/021126 A2 | | 2/2009 | |
| WO | 2009/063833 A1 | | 5/2009 | |
| WO | 2009/063846 A1 | | 5/2009 | |
| WO | 2010/074087 A1 | | 7/2010 | |
| WO | WO-2012048820 A1 | * | 4/2012 | ......... H01L 51/0073 |

OTHER PUBLICATIONS

Morello, "Accurate prediction of emission energies with TD-DFT methods for platinum and iridium OLED materials", Journal of Molecular Modeling, (2017), vol. 23, 174. (Year: 2017).*

Oshiyama, Tomohiro et al., machine translation of JP-2011082238-A (2011) pp. 1-50. (Year: 2011).*

Tanabe et al., Machine translation of JP-2008060379-A (2008) pp. 1-39. (Year: 2008).*

Zhou, Yan, et al., "Selective Oxidfative Cyclization by FeCl3 in the Construction of 10H-Ideno[1,2-b]triphenylene Skeletons in Polycyclic Aromatic Hydrocarbons," The Journal of Organic Chemistry, Sep. 1, 2006, pp. 6822-6828, vol. 71, No. 18, The American Chemical Society.

Mohammed Bourass et al., "DFT theoretical investigations of π-conjugated molecules based on thienopyrazine and different acceptor moieties for organic photovoltaic cells", Journal of Saudi Chemical Society (2016) 20, S415-S425.

* cited by examiner

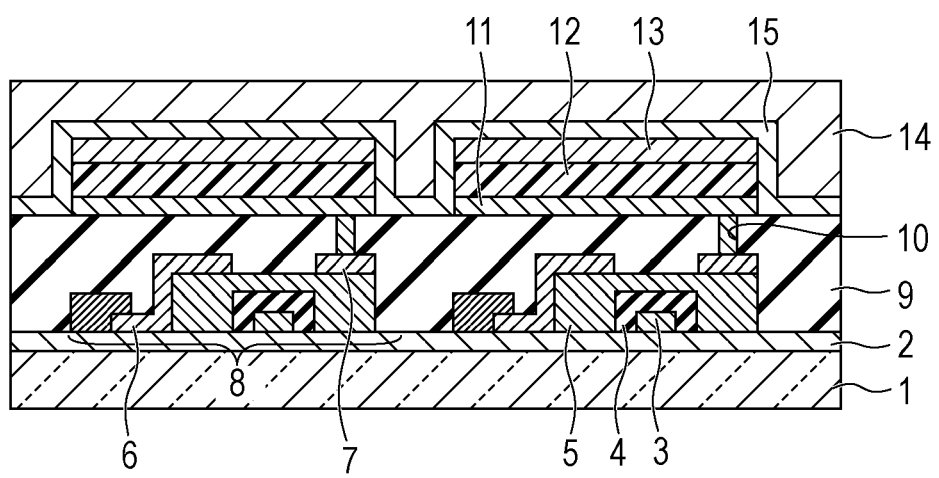

TRIPHENYLENO-BENZOHURAN COMPOUND AND ORGANIC LIGHT EMITTING ELEMENT INCLUDING THE SAME

TECHNICAL FIELD

The present invention relates to a triphenyleno-benzofuran compound and an organic light emitting element including the same.

BACKGROUND ART

An organic light emitting element is an element which includes an anode, a cathode, and an organic compound layer arranged therebetween. In the organic light emitting element, holes and electrons, which are injected from the respective electrodes, recombine in the organic compound layer to generate excitons, and light is emitted when the excitons return to the ground state. The organic light emitting element is also called an organic electroluminescent element or an organic EL element. Recent advances of the organic light emitting element are remarkable, and a thin and lightweight light emitting device having a low drive voltage, various light emitting wavelengths, and high speed response characteristics can be manufactured.

A phosphorescent element is an organic light emitting element which includes a phosphorescent material in the organic compound layer and from which light emission derived from triplet excitons can be obtained. In order to provide a high-performance phosphorescent element, heretofore, new organic compounds have been actively developed.

For example, since the excited triplet ($T_1$) energy of triphenylene is high, triphenylene is used as a basic skeleton of a host material for a phosphorescent element.

In addition, a compound in which indene is condensed with triphenylene has been disclosed in NPL 1. Hereinafter, this compound is called a compound 1.

[Chem. 1]

COMPOUND 1

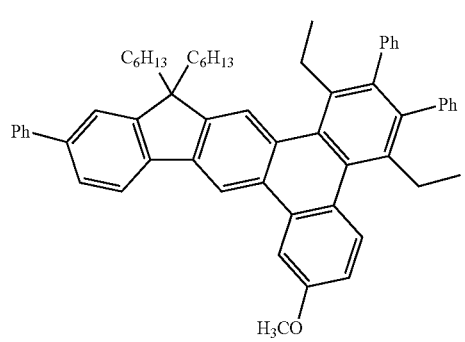

CITATION LIST

Non Patent Literature

NPL 1 The Journal of Organic Chemistry, 71, 6822 (2006)

SUMMARY OF INVENTION

Although the $T_1$ energy of a compound including triphenylene as a basic skeleton is high, the glass transition temperature is low, and hence, the compound is liable to crystallize.

On the other hand, the compound 1 has been disclosed in NPL 1 as a compound which emits fluorescence.

However, since the $T_1$ energy thereof has not been described, it is not clear whether a phosphorescent element including the above compound is useful or not.

The present invention provides a triphenyleno-benzofuran compound which has high $T_1$ energy enough for a green phosphorescent element and a high glass transition temperature (Tg). In addition, the present invention also provides an excellent organic light emitting element which includes the triphenyleno-benzofuran compound as described above and which has a high luminescent efficiency and a long element life.

Accordingly, the present invention provides a triphenyleno-benzofuran compound represented by the following general formula [1].

[Chem. 2]

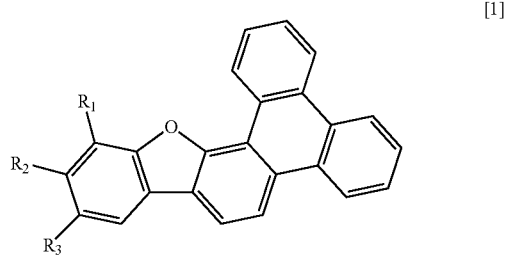

[1]

In the general formula [1], $R_1$ to $R_3$ are each independently selected from a hydrogen atom, a substituted or unsubstituted aryl group, and a substituted or unsubstituted heterocyclic group.

However, at least one of $R_1$ to $R_3$ represents the aryl group or the heterocyclic group.

The aryl group represents a phenyl group, a naphthyl group, a phenanthrenyl group, a fluorenyl group, a triphenylenyl group, or a chrysenyl group.

The heterocyclic group represents a dibenzofuranyl group or a dibenzothienyl group.

Advantageous Effects of Invention

The present invention can provide a triphenyleno-benzofuran compound which has high $T_1$ energy enough for a green phosphorescent element and a high glass transition temperature. In addition, the present invention can also provide an organic light emitting element which includes the compound described above and which has a high luminescent efficiency and a long element life.

BRIEF DESCRIPTION OF DRAWING

The FIGURE is a schematic cross-sectional view showing an organic light emitting element and a switching element connected thereto.

DESCRIPTION OF EMBODIMENTS

A triphenyleno-benzofuran compound is represented by the following general formula [1].

[Chem. 3]

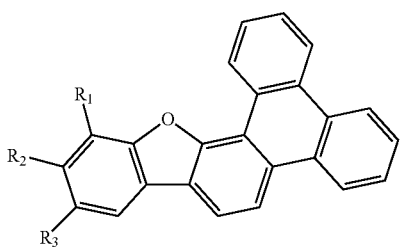

In the general formula [1], $R_1$ to $R_3$ are each independently selected from a hydrogen atom, a substituted or unsubstituted aryl group, and a substituted or unsubstituted heterocyclic group.

However, at least one of $R_1$ to $R_3$ represents the aryl group or the heterocyclic group.

The aryl group represents a phenyl group, a naphthyl group, a phenanthrenyl group, a fluorenyl group, a triphenylenyl group, or a chrysenyl group.

The heterocyclic group represents a dibenzofuranyl group or a dibenzothienyl group.

The phenyl group, the naphthyl group, the phenanthrenyl group, the fluorenyl group, the triphenylenyl group, the chrysenyl group, the dibenzofuranyl group, and the dibenzothienyl group, which are represented by $R_1$ to $R_3$, each may further has a substituent.

The substituent is one of an alkyl group having 1 to 4 carbon atoms, an aryl group, such as a phenyl group, a biphenyl group, a terphenyl group, a naphthyl group, a phenanthrenyl group, a fluorenyl group, a chrysenyl group, or a triphenylenyl group, a dibenzofuranyl group, and a dibenzothienyl group.

Among the substitutes mentioned above, the aryl group, the dibenzofuranyl group, and the dibenzothienyl group each may further has an alkyl group having 1 to 4 carbon atoms.

Properties of Triphenyleno-Benzofuran Skeleton

A triphenyleno-benzofuran skeleton is a skeleton represented by the following structural formula 1. That is, in the general formula [1], the triphenyleno-benzofuran skeleton is a skeleton when the substituents $R_1$ to $R_3$ each represent a hydrogen atom.

[Chem. 4]

Structural formula 1

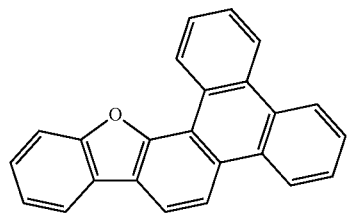

Since the triphenyleno-benzofuran skeleton has a planar structure, molecules thereof are likely to overlap with each other. Hence, carrier movement between the molecules in a solid state efficiently occurs.

From this property, when being used for an organic light emitting element, the triphenyleno-benzofuran compound can be preferably used for a carrier transport layer or as a host of a light emitting layer.

When a compound having a triphenyleno-benzofuran skeleton is used as a host material of a light emitting layer, it is believed that the drive voltage of an organic light emitting element can be decreased.

The reason for this is that carriers injected from an electron transport layer or a hole transport layer are able to efficiently move in this light emitting layer because of the high planarity of the triphenyleno-benzofuran skeleton.

In addition, the triphenyleno-benzofuran skeleton has high $T_1$ energy.

In general, in the case in which the light emitting layer includes a host material and a guest material, and the guest material emits primary light, the $T_1$ energy of the host material is preferably higher than that of the guest material.

Phosphorescence spectrum measurement of a diluted toluene solution of the compound represented by the structural formula 1 was carried out at 77K, and the $T_1$ energy was obtained from the 0-0 band.

The measurement was performed using F-4500 manufactured by Hitachi Co., Ltd.

As a result, the $T_1$ energy is 2.68 eV (462 nm), and this value is sufficiently higher than the emission energy of green and red light.

In this case, the green light in this embodiment indicates light having a maximum peak wavelength of the emission spectrum in a range of 500 to 530 nm, and the red light indicates light having a maximum peak wavelength of the emission spectrum in a range of 600 to 620 nm.

That is, the triphenyleno-benzofuran skeleton has $T_1$ energy higher than that of a luminescent material which emits red light and that of a luminescent material which emits green light.

Therefore, the compound having a triphenyleno-benzofuran skeleton may be preferably used as the host of the light emitting layer in a phosphorescent element using a green to red phosphorescent material.

In addition, since having high $T_1$ energy, the compound having a triphenyleno-benzofuran skeleton enables a luminescent material to emit light with high luminescent efficiency.

Triphenyleno-Benzofuran Compound of the Present Invention

In the triphenyleno-benzofuran compound of the present invention, when a substituent is provided at a specific position of the triphenyleno-benzofuran skeleton, the solubility to a solvent, the sublimability in vacuum deposition, and the amorphous properties in a thin film state can be improved. That is, when these substituents are not provided, the solubility to a solvent, the sublimability in vacuum deposition, and the amorphous properties in a thin film state are not improved.

Therefore, the triphenyleno-benzofuran preferably has a substituent.

In addition, the $T_1$ energy of the compound is influenced by the $T_1$ energy of the substituent thereof.

Hence, attention was paid on the $T_1$ energy of a substituent which might be included in the triphenyleno-benzofuran compound of the present invention.

The $T_1$ energy (equivalent wavelength) of simple substances of main aromatic rings is shown in Table 1. Among those shown in Table 1, benzene, naphthalene, phenanthrene, fluorene, triphenylene, chrysene, dibenzofuran, dibenzothiophene, and pyrene are each preferably used as the substituent.

Furthermore, when the phosphorescent material is a material which emits green light, benzene, naphthalene, phenanthrene, fluorene, triphenylene, chrysene, dibenzofuran, and dibenzothiophene are each a desirable substituent to be bonded to one of positions $R_1$ to $R_3$ of the triphenyleno-benzofuran compound of the present invention.

TABLE 1

| STRUCTURE | $T_1$ ENERGY EQUIVALENT WAVELENGTH |
|---|---|
| BENZENE | 339 nm |
| NAPHTHALENE | 472 nm |
| PHENANTHRENE | 459 nm |
| FLUORENE | 422 nm |
| TRIPHENYLENE | 427 nm |
| CHRYSENE | 500 nm |
| DIBENZOFURAN | 417 nm |
| DIBENZOTHIOPHENE | 415 nm |
| ANTHRACENE | 672 nm |
| PYRENE | 589 nm |

As for the position of the triphenyleno-benzofuran compound of the present invention at which the substituent is provided, the substituent is preferably provided on a carbon atom of the triphenyleno-benzofuran skeleton having a high electron density.

The positions of the triphenyleno-benzofuran skeleton having a high electron density are the positions $R_1$ to $R_3$ shown in the general formula [1]. An electrophilic reaction is likely to occur at the positions $R_1$ to $R_3$.

Hence, the substituent is preferably provided at at least one of the positions $R_1$ to $R_3$ of the general formula [1].

In addition, in the triphenyleno-benzofuran compound of the present invention, in order to suppress a carbon-oxygen bond from dissociation caused by attack on the oxygen atom by an electrophilic reaction, the substituent is preferably provided at the position $R_1$.

The reason for this is that when the substituent is provided at the position $R_1$, the carbon-oxygen bond becomes unlikely to be attacked because of the steric hindrance.

When the substituent is provided at the position $R_1$, the electron density in the compound changes, and the positions $R_2$ and $R_3$ are each no longer a position at which the electron density is high.

Furthermore, in the triphenyleno-benzofuran compound of the present invention, it is more preferable that the substituent is provided at the position $R_1$, and $R_2$ and $R_3$ are each a hydrogen atom. The reason for this is that the sublimability of the above compound is high.

The effect obtained when the triphenyleno-benzofuran compound of the present invention has a substituent can be increased when the above substituent further has an alkyl group. The number of carbon atoms of the alkyl group is preferably 1 to 4. The reason for this is that the sublimability thereof is not degraded.

In addition, when the substituent is provided at at least one of the positions $R_1$ to $R_3$ of the general formula [1], the stability of the triphenyleno-benzofuran compound of the present invention in a thin film state is also improved.

The stability of an organic compound in a thin film state can be evaluated by measuring the glass transition temperature. The stability of the thin film is increased as the glass transition temperature is higher.

The glass transition temperature (Tg) of unsubstituted triphenyleno-benzofuran and that of an example compound A-5 which is the triphenyleno-benzofuran compound of the present invention are shown in Table 2. When the substitute was provided, the glass transition temperature Tg was increased by 73° C., and the thin film stability was improved.

Since the element life is increased, a compound having a high thin film stability is preferably used for a layer of the organic light emitting element.

Therefore, an increase in life of the organic light emitting element can be achieved by using the triphenyleno-benzofuran compound of the present invention as the host material of the light emitting layer.

TABLE 2
| COMPOUND | STRUCTURAL FORMULA | Tg (° C.) |
|---|---|---|
| UNSUBSTITUTED COMPOUND | | 46 |
| A-5 | | 119 |
Examples of Triphenyleno-Benzofuran Compound of the Present Invention
The triphenyleno-benzofuran compounds of the present invention are shown below as groups A to C by way of example.
[Chem. 5]
A-1
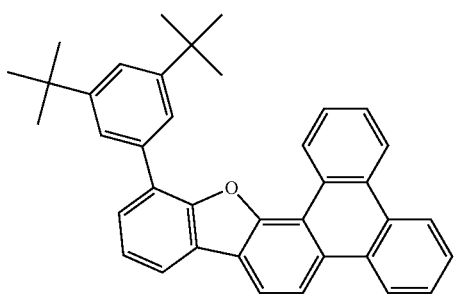
A-2
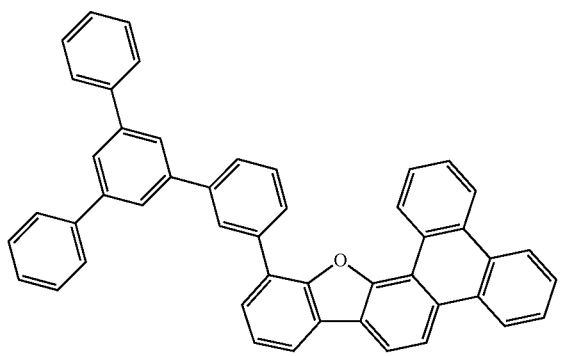
-continued
A-3
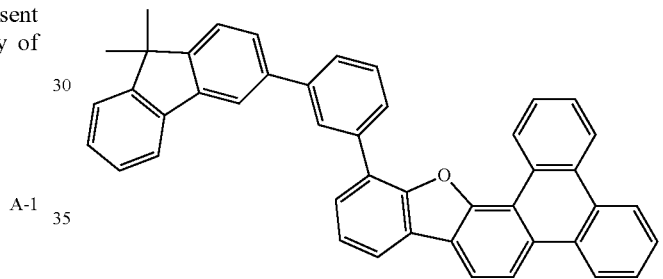
A-4
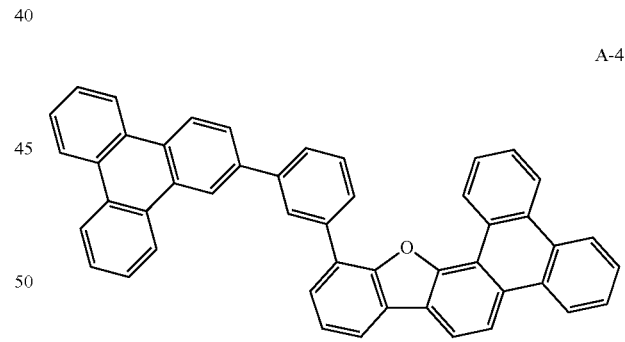
A-5
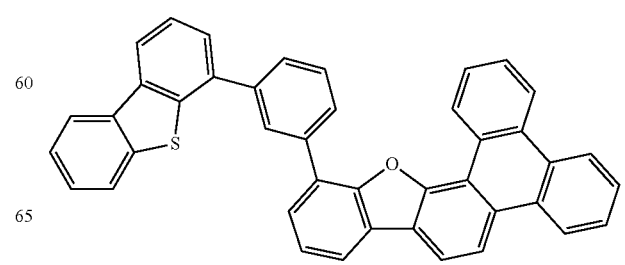

-continued
A-6
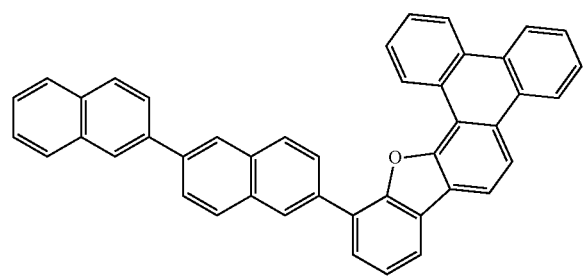
A-7
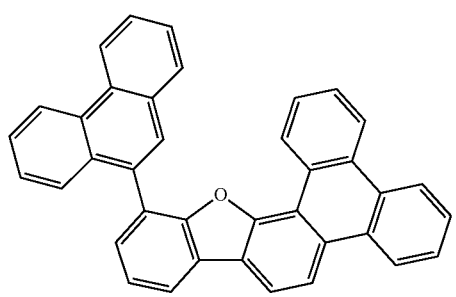
A-8
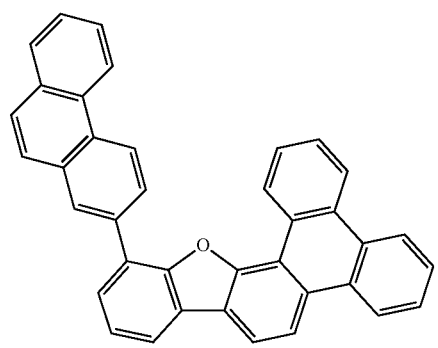
A-9
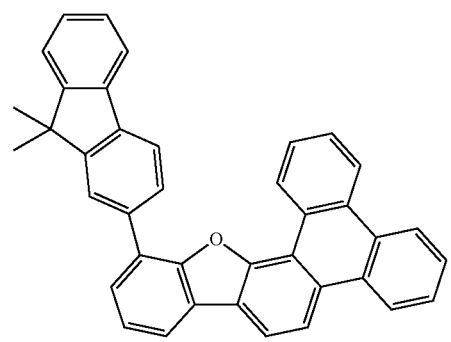
A-10
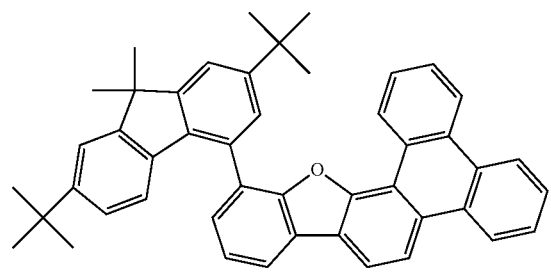
-continued
A-11
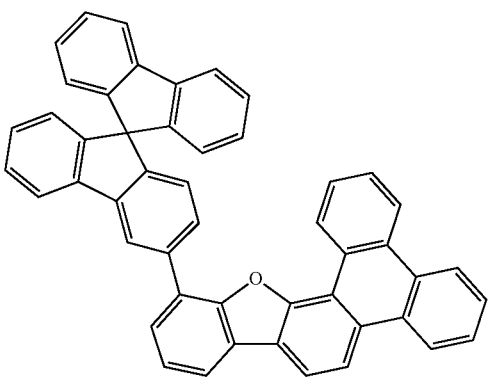
A-12
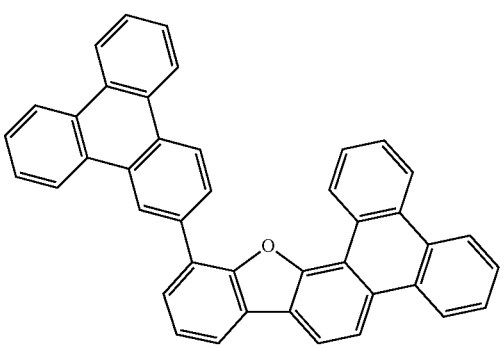
A-13
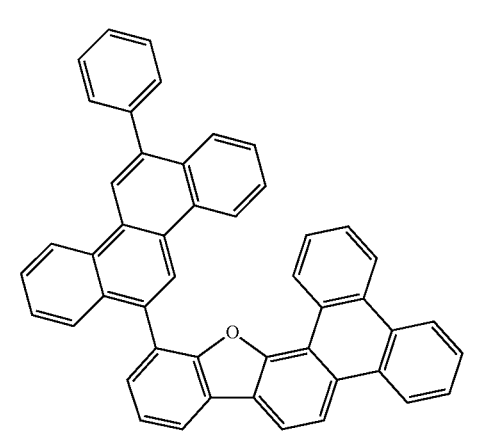
A-14
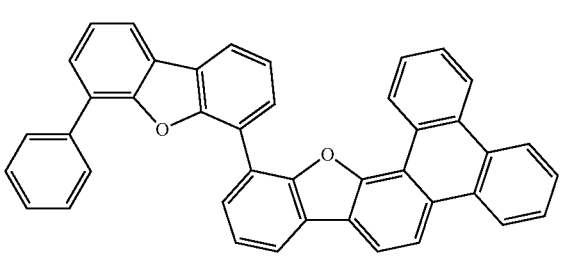

A-15
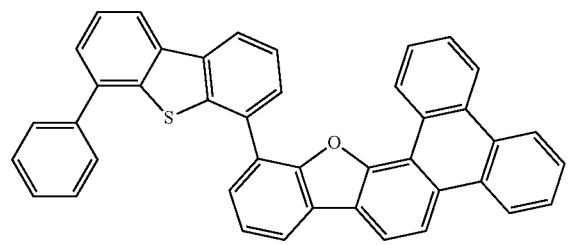
B-5
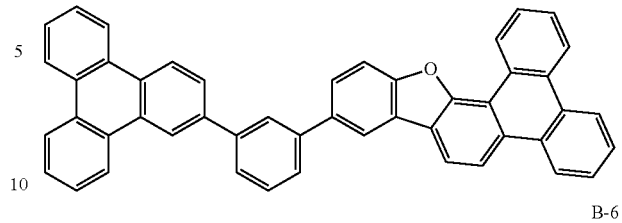
A-16
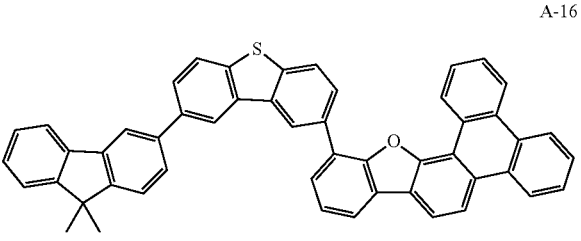
B-6
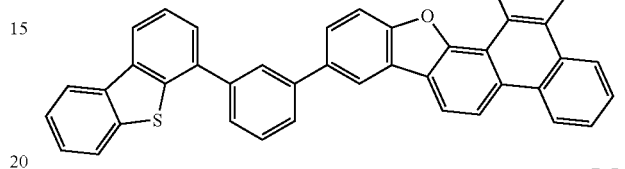
[Chem. 6]
B-1
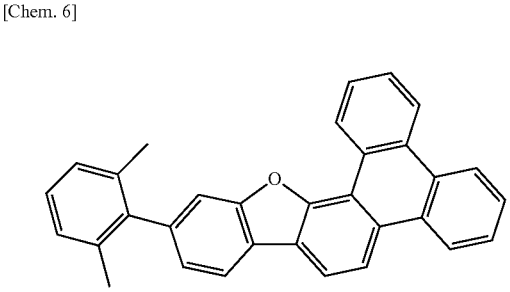
B-7
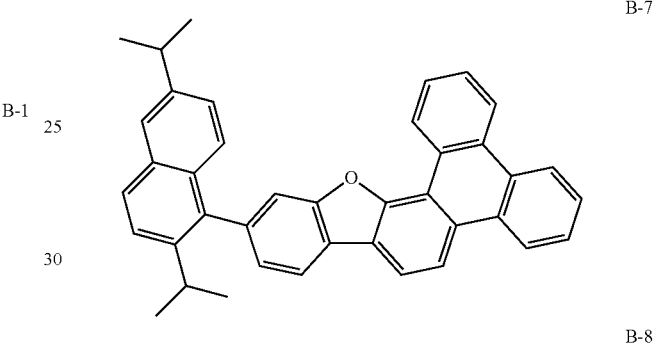
B-2
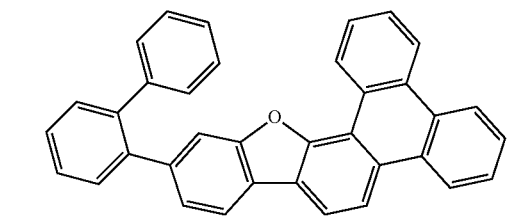
B-8
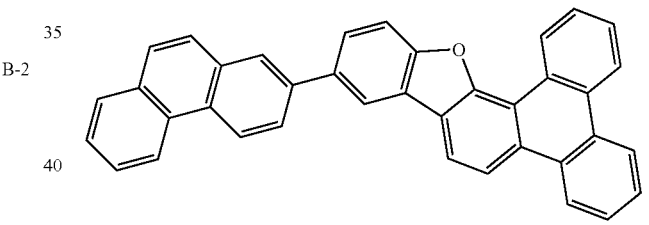
B-3
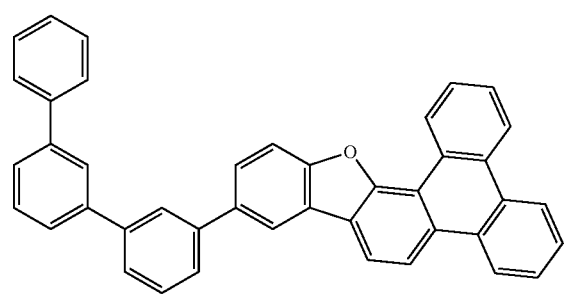
B-9
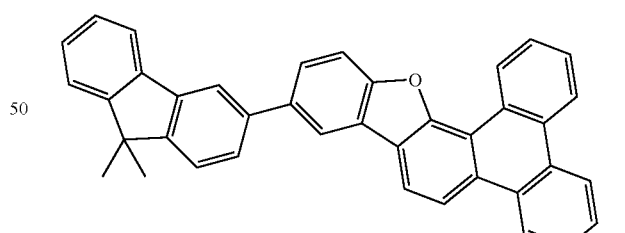
B-4
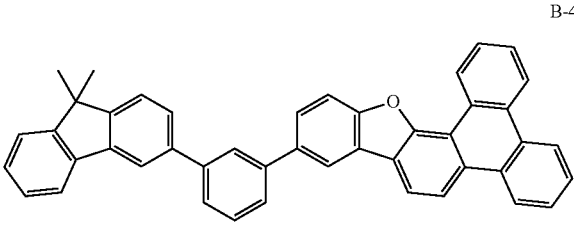
B-10
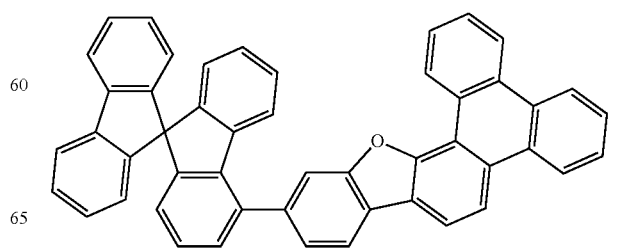

-continued

B-11
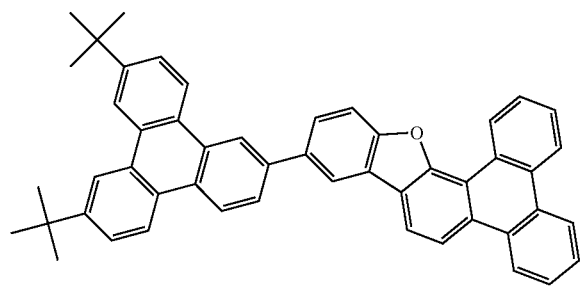

B-12
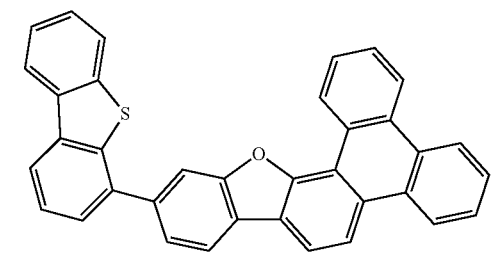

[Chem. 7]

C-1
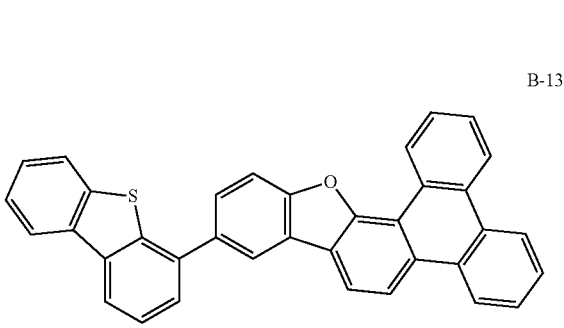

B-13
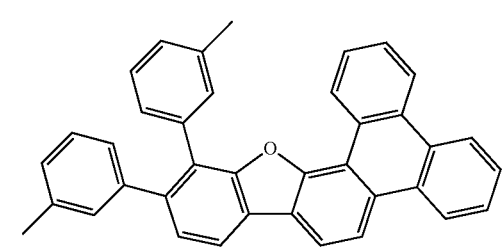

C-2
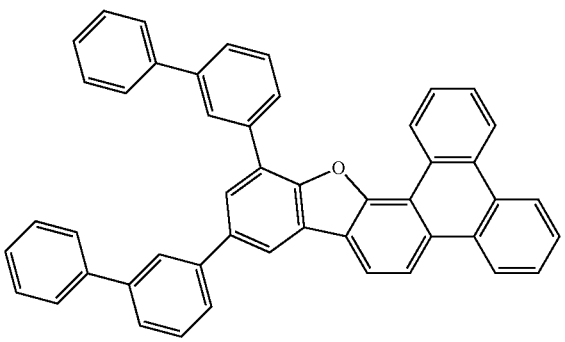

-continued

C-3
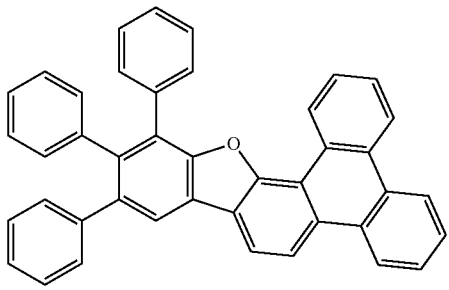

C-4
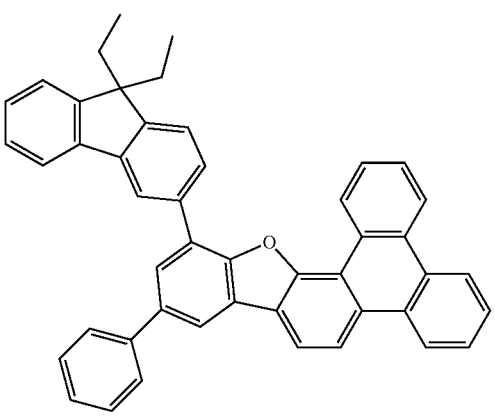

C-5
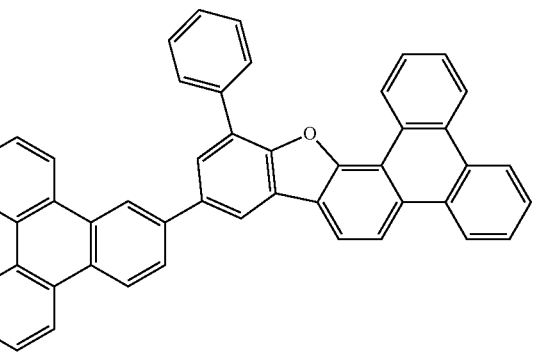

C-6
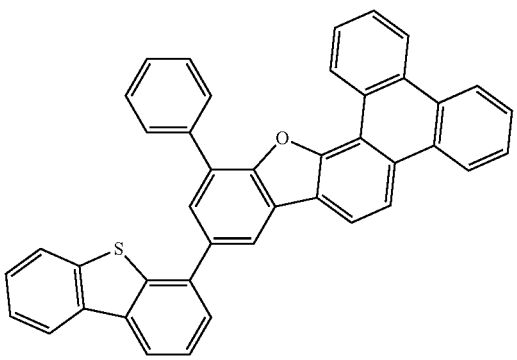

Properties of Example Compounds

The example compounds shown in the group A are each a compound having only one substituent at the position $R_1$ of the general formula [1]. These compounds each have good balance among chemical stability, thin film stability, and sublimability, and high $T_1$ energy of the triphenyleno-benzofuran skeleton can be maintained.

Therefore, in particular, the example compounds in the group A are each preferably used as the host material of a light emitting layer of a phosphorescent element which emits green light.

The example compounds shown in the group B are each a compound having a substituent at the position $R_2$ or $R_3$ of the general formula [1]. When the position and the type of substituent are variously changed, the properties can be finely adjusted. In addition, when the substituent is provided at the position $R_3$ which is an active site, the compound having this substitute is stable.

The example compounds shown in the group C are each a compound having at least two substituents at at least two of the positions $R_1$ to $R_3$ of the general formula [1]. Since protecting the active site by the bond and/or the steric hindrance, in particular, the compounds having at least two substituents described above are chemically stable.

Description of Synthetic Route

One example of a synthetic route of the triphenyleno-benzofuran compound of the present invention will be described. Hereinafter, a synthetic scheme will be described.

First, by a Suzuki coupling carried out using commercial 4-dibenzofuranyl boronic acid and a 1,2-dihalogenobenzene ($X_1$, $X_2$=I, Br, Cl), a monohalogen intermediate is synthesized.

Subsequently, a boronic acid derivative (R=H or an alkyl group) is synthesized by metal catalytic reaction or a lithiation reaction.

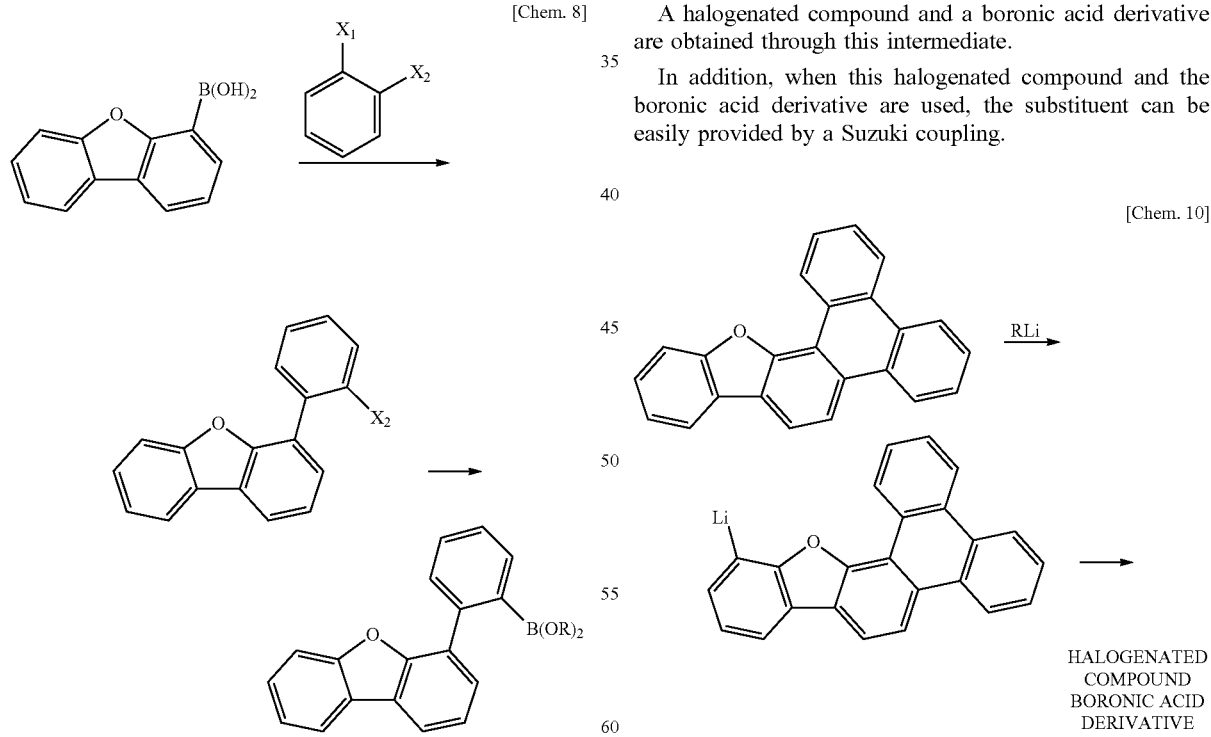

[Chem. 8]

A precursor of triphenyleno-benzofuran is further synthesized by coupling between the boronic acid derivative and a 1,2-dihalogenobenzene.

In addition, triphenyleno-benzofuran is obtained by cyclizing this precursor by a Heck reaction.

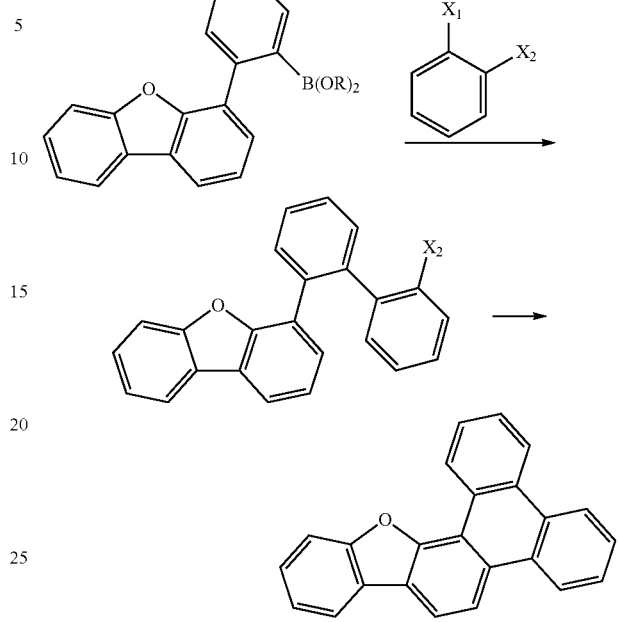

[Chem. 9]

If an alkyllithium reagent is allowed to act on triphenyleno-benzofuran, lithiation is selectively performed at the position $R_1$ of the general formula [1].

A halogenated compound and a boronic acid derivative are obtained through this intermediate.

In addition, when this halogenated compound and the boronic acid derivative are used, the substituent can be easily provided by a Suzuki coupling.

[Chem. 10]

HALOGENATED COMPOUND
BORONIC ACID DERIVATIVE

In addition, there is also a method in which after a dibenzofuran derivative with a substituent already having a reactive functional group and/or an aromatic ring is prepared, the triphenyleno-benzofuran skeleton is synthesized using the same.

For example, when 2-, or 3-chlorodibenzofuran is used as a starting material, triphenyleno-benzofuran having a chlorine atom at the position $R_3$ or $R_2$ of the general formula [1] can be obtained.

[Chem. 11]

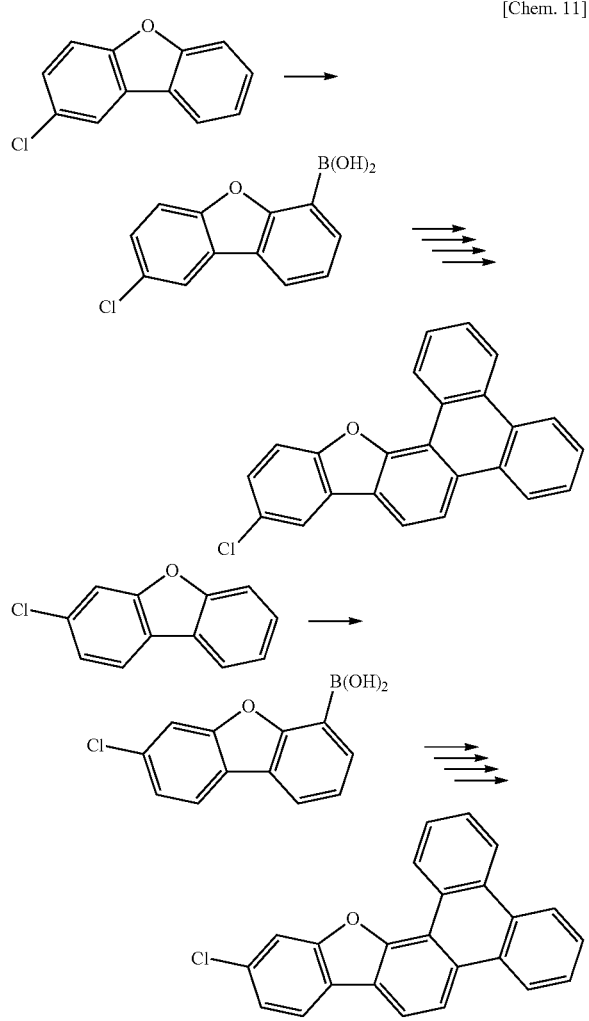

When the above basic reactions are used in various combination, a desired substituent can be provided at any one of the positions $R_1$ to $R_3$ of the general formula [1].

In addition, a plurality of arrows of the above reaction formula indicates multistage reactions which are not shown in the FIGURE. The contents of the reactions not shown indicate the combination of the above reactions.

Properties of Organic Light Emitting Element According to this Embodiment

Next, an organic light emitting element according to this embodiment will be described.

The organic light emitting element according to this embodiment is an organic light emitting element which includes a pair of electrodes, an anode and a cathode, facing each other and at least one organic compound layer arranged therebetween.

A layer having a phosphorescent material among the organic compound layers is a light emitting layer. In addition, in the organic light emitting element of the present invention, the above organic compound layer contains the triphenyleno-benzofuran compound represented by the general formula [1].

In the organic light emitting element according to this embodiment, the number of the organic compound layers may be one or two or more. The plurality of layers are layers appropriately selected from a hole injection layer, a hole transport layer, an electron blocking layer, a light emitting layer, a hole blocking layer, an electron transport layer, an electron injection layer, an exciton diffusion blocking layer, and the like.

Of course, a plurality of layers may be selected from the above group and may be used in combination. For example, an organic light emitting element which has a pair of electrodes, a hole injection layer, a hole transport layer, a light emitting layer, an electron transport layer, and an electron injection layer may be mentioned.

In addition, a plurality of light emitting layers may be provided so that respective elements emit different types of color light.

A light emitting element having a plurality of light emitting layers may have a plurality of light emitting layers between a pair of electrodes. For example, there may be mentioned a structure in which light emitting layers respectively emitting red, green, and blue light are laminated between an anode and a cathode.

However, the structure of the organic light emitting element according to this embodiment is not limited thereto. For example, there may be used various layer structures in which an insulating layer is provided at the interface between the electrode and the organic compound layer, in which an adhesion layer or an interference layer is provided, and in which the electron transport layer or the hole transport layer is formed from two layers having different ionization potentials.

As element configurations in the cases described above, any one of a so-called top emission method in which light is extracted from a side opposite to the substrate, a so-called bottom emission method in which light is extracted from a substrate side, and a dual extraction method may be used.

In the organic light emitting element according to this embodiment, the triphenyleno-benzofuran compound may be included in any layer. In particular, the triphenyleno-benzofuran compound is preferably used for the hole transport layer, the electron transport layer, the hole/exciton blocking layer, and/or the light emitting layer. The triphenyleno-benzofuran compound is more preferably used as the host material of the light emitting layer.

The light emitting layer of the organic light emitting element according to this embodiment may include a plural types of organic compounds. As the plural types of organic compounds, for example, the host material and the guest material may be mentioned.

In this case, the host material is a compound having the highest weight ratio among the organic compounds forming the light emitting layer. The guest material is a compound which has a weight ratio smaller than that of the host material among the organic compounds forming the light emitting layer and which performs primary light emission. An assistant material is a compound which has a weight ratio smaller than that of the host material among the organic compounds forming the light emitting layer and which assists light emission of the guest material. The assistant material may also be called a second host material in some cases.

The triphenyleno-benzofuran compound of the present invention may be used as the host material. When at least two types of host materials are present, the triphenyleno-benzofuran compound of the present invention may have a smaller weight ratio than that of the other host materials.

That is, the triphenyleno-benzofuran compound of the present invention may function as the assistant material.

The concentration of the guest material to the host material of the light emitting layer of the organic light emitting element according to this embodiment is, on the basis of the whole amount of the materials forming the light emitting layer, 0.01 to 50 percent by weight and preferably 0.1 to 20 percent by weight. The concentration is more preferably 10 percent by weight or less. The reason for this is to suppress the concentration quenching.

In addition, the guest material may be uniformly included in the whole layer formed of the host material, may be included to form a concentration gradient, or may be partially included in a specific region to form a region of a host material layer containing no guest material.

The light emitted from the phosphorescent material is preferably green to red light having a maximum emission peak wavelength of 500 to 620 nm. More preferably, the light is green light having a wavelength in a range of 500 to 530 nm.

In the phosphorescent element, in order to suppress a decrease in luminescent efficiency from $T_1$ of the host material caused by nonradiative deactivation, the $T_1$ energy of the host material is preferably higher than the $T_1$ energy of the phosphorescent material functioning as the guest material.

The T1 energy of the triphenyleno-benzofuran skeleton which is a main structure of the triphenyleno-benzofuran compound of the present invention is 462 nm.

This value is higher than the $T_1$ energy of the phosphorescent material which emits green light. Therefore, if the triphenyleno-benzofuran compound of the present invention is used for the light emitting layer of a phosphorescent element which emits green to red light, a phosphorescent element having a high luminescent efficiency can be obtained.

When the triphenyleno-benzofuran compound of the present invention is used as the host material of the light emitting layer, as the phosphorescent material used as the guest material, for example, metal complexes, such as an iridium complex, a platinum complex, a rhenium complex, a copper complex, a europium complex, and a ruthenium complex, may be mentioned.

Among those mentioned above, an iridium complex having strong phosphorescent light emission is preferable. In addition, in order to assist transfer of excitons and carriers, the light emitting layer may include a plurality of phosphorescent materials.

Although examples of the iridium complex used as the phosphorescent material of the present invention are shown below, the present invention is not limited to thereto.

[Chem. 12]

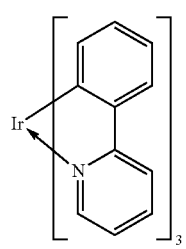

Ir-1

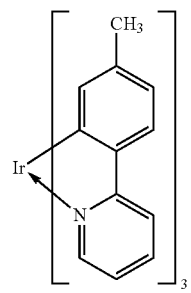

Ir-2

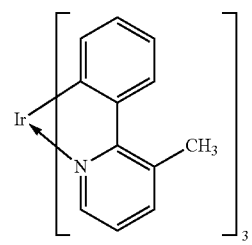

Ir-3

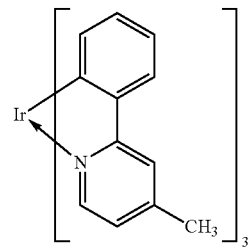

Ir-4

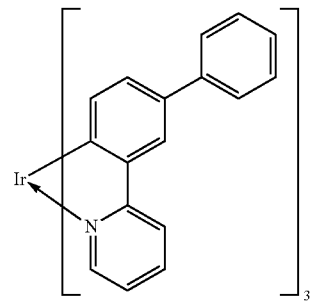

Ir-5

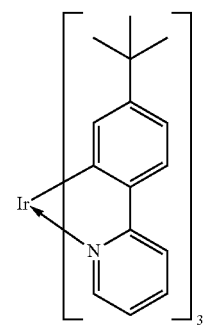

Ir-6

Ir-7 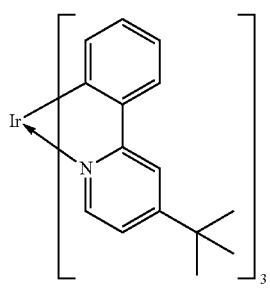
Ir-8 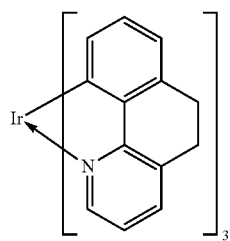
Ir-9 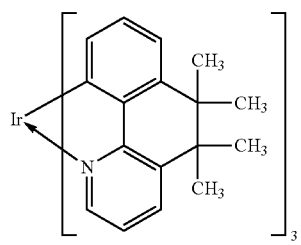
Ir-10 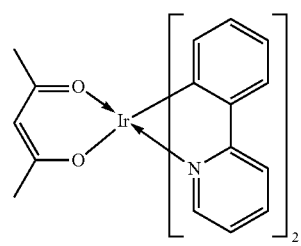
Ir-11 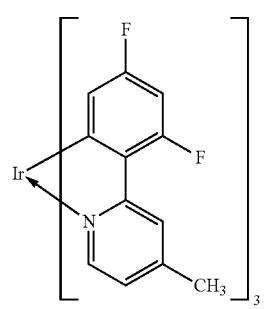
Ir-12 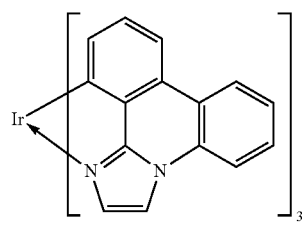
Ir-13 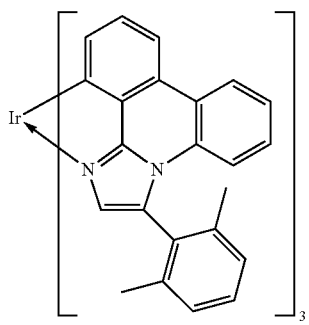
Ir-14 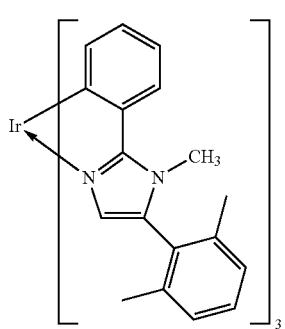
Ir-15 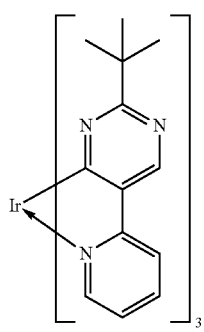
Ir-16 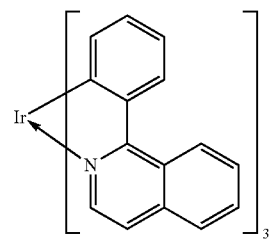
Ir-17 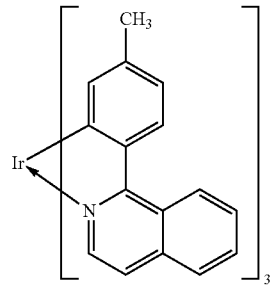

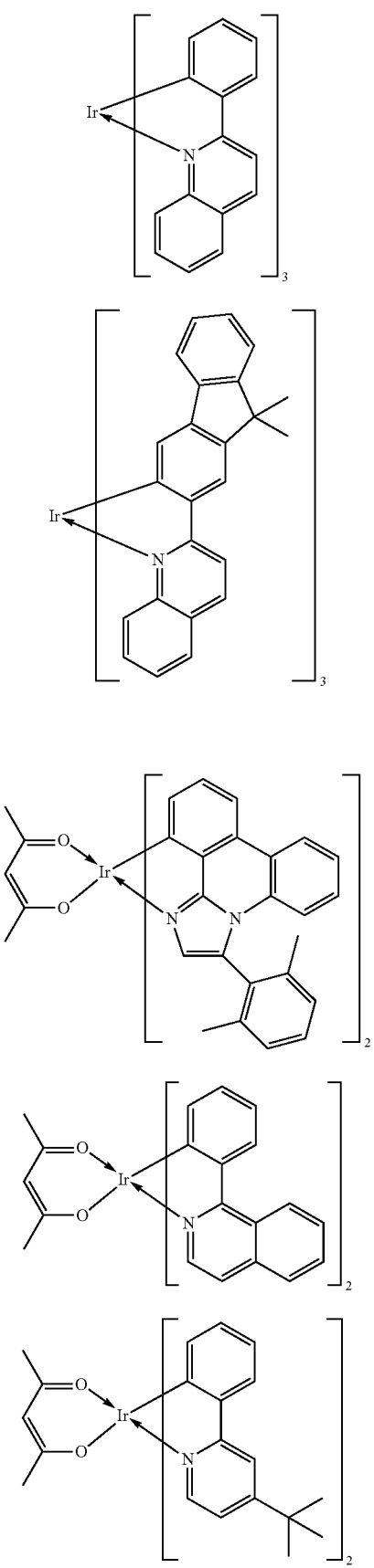
Ir-18
Ir-19
Ir-20
Ir-21
Ir-22
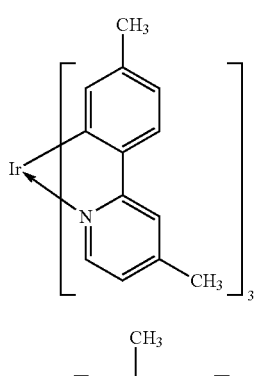
Ir-23
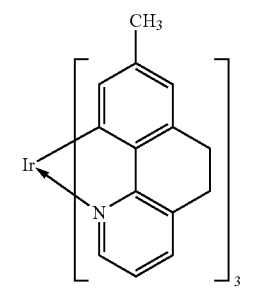
Ir-24
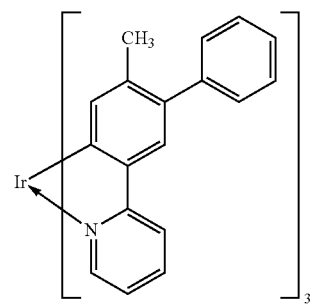
Ir-25
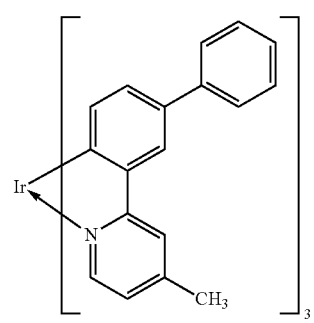
Ir-26
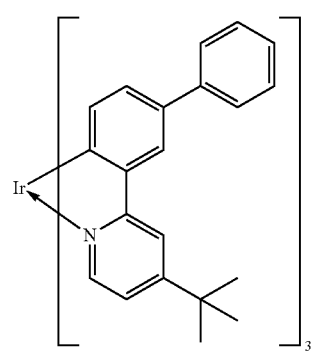
Ir-27

Besides the compounds of the present invention, the organic light emitting element according to this embodiment may also use known low molecular and high molecular compounds, if needed.

In more particular, for example, a hole injection compound or a hole transport compound, a host material or a luminescent compound, or an electron injection compound or an electron transport compound may be used together.

Hereinafter, examples of these compounds will be described.

As a hole injection/transport material, a material having a high hole mobility is preferable so that holes from the anode are easily injected thereinto and so that injected holes are transferred to the light emitting layer.

As the low molecular and high molecular material having a hole injection/transport ability, for example, a triarylamine derivative, a phenylenediamine derivative, a stilbene derivative, a phthalocyanine derivative, a porphyrin derivative, a poly(vinyl carbazole), a poly(thiophene), and other conductive polymers may be mentioned.

As the host material other than the triphenyleno-benzofuran compound of the present invention, for example, there may be mentioned a m-phenylene derivative, a condensed ring compound (such as a fluorene derivative, a naphthalene derivative, a triphenylene derivative, a phenanthrene derivative, or a chrysene derivative), a furan derivative, a thiophene derivative, a carbazole derivative, an arylsilane derivative, and an organic aluminum complex.

As the luminescent material primarily responsible for light emission, besides the phosphorescent guest materials or the derivatives thereof, for example, a condensed ring compound (such as a fluorene derivative, a naphthalene derivative, a pyrene derivative, a perylene derivative, a tetracene derivative, an anthracene derivative, or rubrene), a quinacridone derivative, a coumarin derivative, a stilbene derivative, an organic aluminum complex, such as tris(8-quinolinolato)aluminum, an organic beryllium complex, and a polymer derivative, such as a poly(phenylenevinylene) derivative, a poly(fluorene) derivative, or a poly(phenylene) derivative, may be mentioned.

As an electron injection/transport material, in consideration of the balance with the hole mobility of the hole injection/transport material, a material may be freely selected from those into which electrons can be easily injected from the cathode and which can transport injected electrons to the light emitting layer.

As a material having an electron injection/transport ability, for example, an oxadiazole derivative, an oxazole derivative, a pyrazine derivative, a triazole derivative, a triazine derivative, a quinoline derivative, a quinoxaline derivative, a phenanthroline derivative, and an organic aluminum complex may be mentioned.

As an anode material, a material having a work function as high as possible is preferable.

For example, metals, such as gold, platinum, silver, copper, nickel, palladium, cobalt, selenium, vanadium, and tungsten, alloys formed from the metals mentioned above in combination, and metal oxides, such as tin oxide, zinc oxide, indium oxide, indium tin oxide (ITO), and indium zinc oxide, may be used.

In addition, conductive polymers, such as a polyaniline, a polypyrrole, and a polythiophene, may also be used.

These electrode materials may be used alone, or at least two types thereof may be used in combination. In addition, the anode may be formed either from a single layer or a plurality of layers.

On the other hand, as a cathode material, a material having a low work function is preferably used. For example, alkali metals such as lithium, alkaline earth metals such as calcium, and metals, such as aluminum, titanium, manganese, silver, lead, and chromium, may be mentioned. Alternatively, alloys formed from those metals in combination may also be used.

For example, magnesium-silver, aluminum-lithium, and aluminum-magnesium may be used. Metal oxides, such as indium tin oxide (ITO), may also be used. These electrode materials may be used alone, or at least two types thereof may be used in combination. In addition, the cathode may be formed either from a single layer or a plurality of layers.

In the organic light emitting element according to this embodiment, the layer including the triphenyleno-benzofuran compound of the present invention and the layer including the other organic compound are formed by the following methods.

As the method of forming the organic compound layer, for example, there may be mentioned a vacuum deposition method, an ionization deposition method, a sputtering method, a plasma deposition method, or a known coating method (such as spin coating, dipping, a casting method, an LB method, or an ink jet method) using an organic compound dissolved in an appropriate solvent.

When the layer is formed, for example, by a vacuum deposition method or a solution coating method, for example, crystallization is not likely to occur, and a film having excellent aging stability is obtained. In addition, when a coating method is used for film formation, a film may also be formed in combination with a suitable binder resin.

As the binder resin mentioned above, although a poly(vinyl carbazole) resin, a polycarbonate resin, a polyester resin, an ABS resin, an acrylate resin, a polyimide resin, a phenol resin, an epoxy resin, a silicone resin, a urea resin, and the like may be mentioned, the binder resin is not limited thereto.

In addition, as the binder resin, a homopolymer or a copolymer may only be used, or at least two types thereof may also be used in combination. Furthermore, additives, such as a known plasticizer, antioxidant, and ultraviolet absorber, may also be used, if needed.

Application of Organic Light Emitting Element According to this Embodiment

The organic light emitting element according to this embodiment may be used for a display device and a lighting device. In addition, the organic light emitting element according to this embodiment may also be used, for example, for an exposure light source of an image forming device of an electrophotographic system and a backlight of a liquid crystal display device.

The display device has the organic light emitting element according to this embodiment in a display portion. This display portion includes a plurality of pixels. The pixels each have the organic light emitting element according to this embodiment and a TFT element as one example of a switching element controlling the luminescent brightness. The switching element is connected to the anode or the cathode of this organic light emitting element and a drain electrode or a source electrode of the thin film transistor.

The display device may be used as an image display device of a personal computer (PC), a head mount display, a mobile phone, or the like. As an image to be displayed, any image, such as a two-dimensional image or a three-dimensional image, may be displayed.

The display device may be an image output device which has an image input portion to input information from an area CCD, a linear CCD, a memory card, or the like, and which outputs an inputted image on the display portion.

The image output device may be a digital camera having an imaging optical system in which the image input portion is formed of an image sensor, such as a CCD sensor.

The display device may have an input function which can perform an input by touching an output image. For example, a touch-panel function may be mentioned.

In addition, the display device may be used for a display portion of a multifunctional printer.

The organic light emitting element according to this embodiment may also be used for a lighting device. This lighting device has the organic light emitting element according to this embodiment and an inverter circuit connected thereto.

The color of light emitted from the lighting device according to this embodiment may be white, natural white, and any other colors.

Next, the display device having the organic light emitting elements according to this embodiment will be described with reference to the FIGURE.

The FIGURE is a schematic cross-sectional view showing the organic light emitting element according to this embodiment and a TFT element, which is one example of a switching element, connected the above organic light emitting element. In this FIGURE, two sets each including the organic light emitting element and the TFT element are shown. Hereinafter, the structure will be described in detail.

The display device shown in the FIGURE includes a substrate 1 formed of a glass or the like and a dampproof film 2 provided thereon to protect the TFT element or the organic compound layer. In addition, reference numeral 3 indicates a metal gate electrode. Reference numeral 4 indicates a gate insulating film, and reference numeral 5 indicates a semiconductor layer.

A thin film transistor 8 includes the semiconductor layer 5, a drain electrode 6, and a source electrode 7. An insulating film 9 is provided on an upper portion of the thin film transistor 8, and an anode 11 of the organic light emitting element and the source electrode 7 are connected to each other through a contact hole 10.

The display device is not limited to that described above and may have any structure as long as the anode or the cathode is connected to one of the source electrode and the drain electrode of the thin film transistor.

Since this FIGURE is simplified, an organic compound layer 12 is shown as one layer; however, a plurality of organic compound layers may be provided. On the cathode 13, a first protective layer 14 and a second protective layer 15 are provided to suppress degradation of the organic light emitting element.

In the display device according to this embodiment, the switching element is not particularly limited, and a transistor or an MIM element may be used. As the transistor, for example, a thin film transistor using single crystal silicon or an amorphous-silicon type transistor element may be used. The thin film transistor is also called a TFT element.

The luminescent brightness of the organic light emitting element is controlled by the switching element. When a plurality of organic light emitting elements is provided on the plane, an image can be displayed by the luminescent brightness of each organic light emitting element.

In addition, the control may also be performed in such a way that active matrix drivers are formed on a Si substrate, and the organic light emitting elements are provided thereon. The structure may be selected depending on the fineness, and for example, when the fineness is approximately QVGA, the structure in which organic light emitting elements are provided on a Si substrate is preferable.

When the display device using the organic light emitting elements according to this embodiment is driven, stable display with excellent image quality can be performed for a long time.

EXAMPLES

Hereinafter, examples will be described. However, the present invention is not limited to the following examples.

Example 1

Synthesis of Intermediate 1

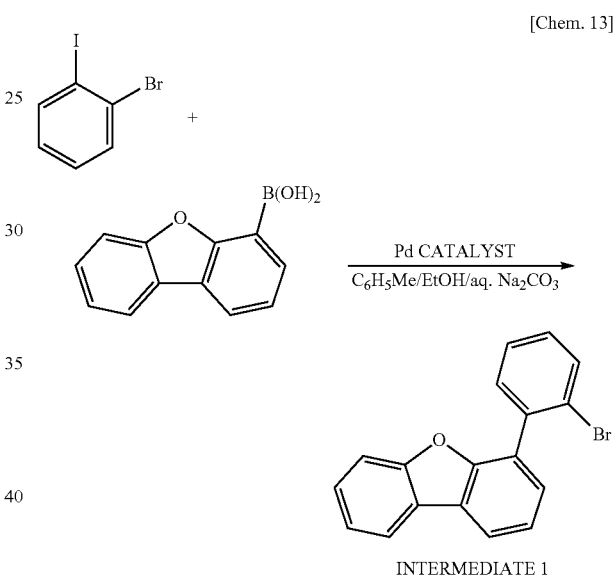

[Chem. 13]

INTERMEDIATE 1

The following reagents and solvents were charged in a 200-ml eggplant flask.

2-Bromoiodobenzene (manufactured by Tokyo Kasei Kogyo Co., Ltd.): 5.0 g (18 mmol)

4-Dibenzofuranyl boronic acid (manufactured by Sigma-Aldrich Co.): 3.8 g (18 mmol)

Tetrakis(triphenylphosphine)palladium(0): 1.0 g (0.90 mmol)

Toluene: 50 ml

Ethanol: 10 ml

2M Sodium carbonate aqueous solution: 23 ml

This reaction solution was stirred and heated at 80° C. for 6 hours in a nitrogen atmosphere. After the reaction was completed, an organic layer was separated, was dried with magnesium sulfate, and was then filtrated.

The solvent of the filtrate thus obtained was distilled off under reduced pressure, and a viscous product was refined by a silica gel column (chloroform:heptane=1:3), so that 3.9 g of an intermediates 1 was obtained (yield: 68%).

Synthesis of Intermediate 2

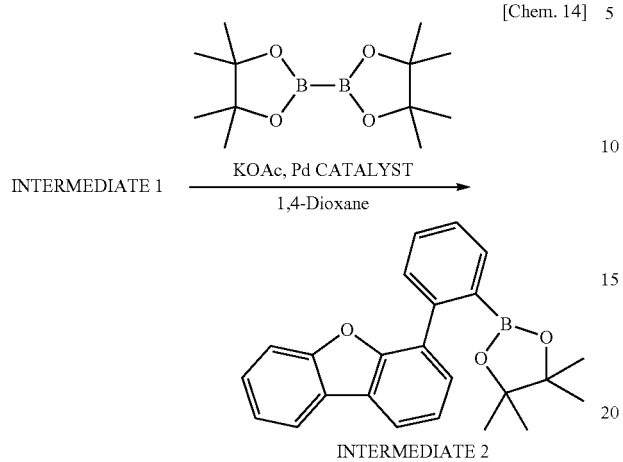

The following reagents and solvent were charged in a 100-ml eggplant flask.

Intermediate 1: 3.9 g (12 mmol)
Bis(pinacolato)diboron: 3.4 g (13 mmol)
[1,1'-Bis(diphenylphosphino)ferrocene]palladium(II)dichloride
dichloromethane adduct: 0.98 g (1.2 mmol)
Potassium acetate: 2.1 g (22 mmol)
1,4-Dioxane (dehydrated): 40 ml This reaction solution was stirred and refluxed by heating for 5 hours in a nitrogen atmosphere. After the reaction was completed, a precipitated salt was removed by filtration. The solvent of the filtrate thus obtained was distilled off under reduced pressure, and a precipitated solid was refined by a silica gel column (ethyl acetate:heptane=1:5), so that 3.4 g of an intermediates 2 was obtained (yield: 76%).

Synthesis of Intermediate 3

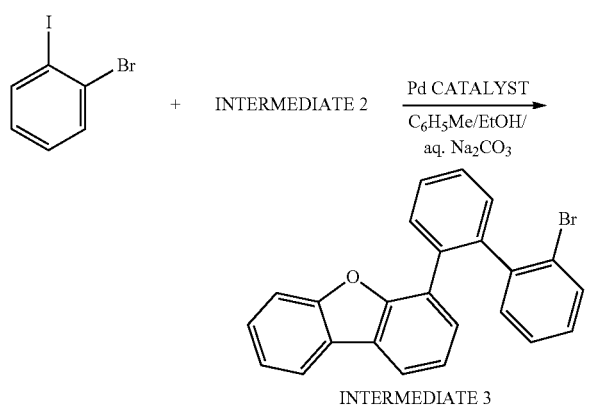

The following reagents and solvents were charged in a 100-ml eggplant flask.

2-Bromoiodobenzene: 2.6 g (9.1 mmol)
Intermediate 2: 3.4 g (9.1 mmol)
Tetrakis(triphenylphosphine)palladium(0): 0.53 g (0.46 mmol)
Toluene: 30 ml
Ethanol: 6 ml
2M Sodium carbonate aqueous solution: 12 ml This reaction solution was stirred and heated at 80° C. for 5 hours in a nitrogen atmosphere. After the reaction was completed, an organic layer was separated, was dried with magnesium sulfate, and was then filtrated. The solvent of the filtrate thus obtained was distilled off under reduced pressure, and a viscous product was refined by a silica gel column (chloroform:heptane=1:3), so that 2.1 g of an intermediates 3 was obtained (yield: 59%).

Synthesis of Triphenyleno-Benzofuran

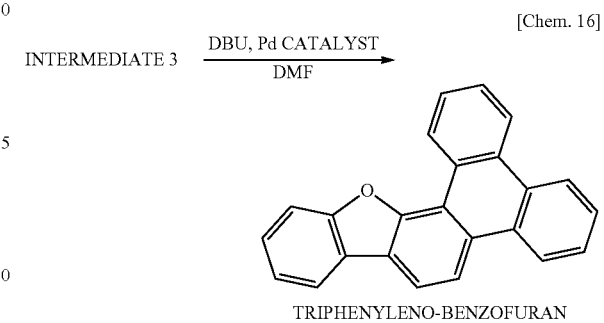

The following reagents and solvent were charged in a 100-ml eggplant flask.

Intermediate 3: 2.1 g (5.4 mmol)
1,8-Diazabicyclo[5.4.0]-7-undecene (DBU): 8.2 g (54 mmol)
Tetrakis(triphenylphosphine)palladium(0): 0.62 g (0.54 mmol)
Dimethylformamide (DMF) (dehydrated): 15 ml This reaction solution was stirred and heated at 160° C. for 18 hours in a nitrogen atmosphere. After the reaction was completed, water was added at room temperature, so that a solid was precipitated. A solid obtained by filtration was washed with water and methanol and was then refined by a silica gel column (chloroform:heptane=1:3), so that 1.0 g of triphenyleno-benzofuran was obtained (yield: 65%).

By MALDI-TOF MS (matrix-assisted laser desorption-ionization time-of-flight mass spectrometry), 318.1 which was M+ of this compound was confirmed.

Furthermore, the structure of this compound was confirmed using $^1$H-NMR measurement.

$^1$H-NMR (CDCl$_3$, 500 MHz) delta (ppm): 9.93 (1H, dd), 8.79-8.71 (4H, m), 8.24 (1H, d), 8.10 (1H, d), 7.87-7.82 (2H, m), 7.78-7.74 (1H, m), 7.73-7.68 (2H, m), 7.58-7.54 (1H, m), 7.47-7.43 (1H, m)

In addition, the T$_1$ energy was measured by the following method.

By using a diluted toluene solution ($1 \times 10^{-5}$ M) of triphenyleno-benzofuran, the phosphorescence spectrum was measured at an excitation wavelength of 350 nm in an Ar atmosphere at 77K using F-4500 manufactured by Hitachi Co., Ltd. The T$_1$ energy equivalent wavelength obtained from the peak wavelength of the 0-0 band (the first luminescence peak) of the obtained phosphorescence spectrum was 462 nm.

In addition, the glass transition temperature (Tg) of triphenyleno-benzofuran measured using "DSC 204 F1" manufactured by NETZSCH was 46° C.

Synthesis of Intermediate 4

[Chem. 17]

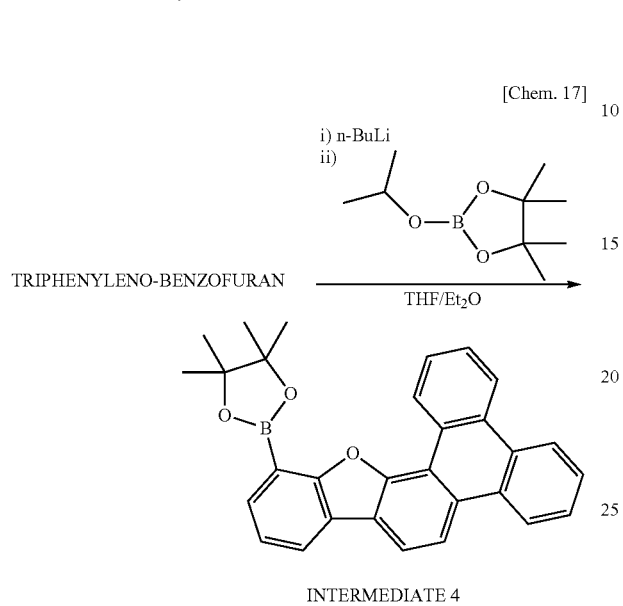

INTERMEDIATE 4

The following reagent and solvents were charged in a 100-ml eggplant flask.
Triphenyleno-benzofuran: 0.60 g (1.9 mmol)
Tetrahydrofuran (THF): 25 ml
Diethyl ether (Et$_2$O): 20 ml To this reaction solution, 3.5 ml of 1.6 M n-BuLi solution (hexane) was dripped at 0° C. in a nitrogen atmosphere. When the solution was returned to room temperature and was stirred for 1 hour, the solution was changed to a dark green color.

The solution was again cooled to 0° C., and 1.3 ml (6.6 mmol) of 2-isopropoxy-4,4,5,5-tetramethyl-1,3,2-dioxaborolane was added thereto.

After a white suspension thus obtained was further stirred for 30 minutes at room temperature, 20 ml of toluene and 20 ml of water were added, and two-layer extraction was performed. An organic layer was separated, was dried with magnesium sulfate, and was then filtered.

The solvent of the filtrate thus obtained was distilled off under reduced pressure, and a precipitated solid was refined by a silica gel column (ethyl acetate:heptane=1:5), so that 0.61 g of an intermediates 4 was obtained (yield: 72%).

Synthesis of Intermediate 5

[Chem. 18]

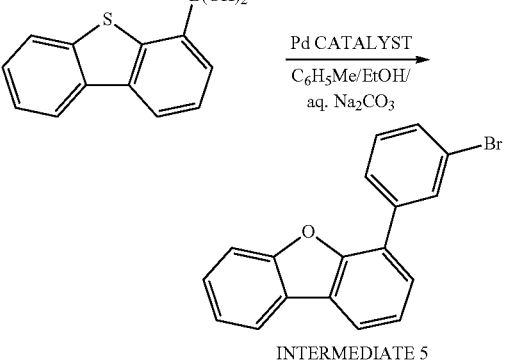

INTERMEDIATE 5

An intermediate 5 was obtained by a method similar to that for synthesis of the intermediate 1 except that 2-bromoiodobenzene and 4-dibenzofuranyl boronic acid, which were used in Example 1, were changed to 1,3-dibromobenzene (manufactured by Tokyo Kasei Kogyo Co., Ltd.) and 4-dibenzothienyl boronic acid (manufactured by Sigma-Aldrich Co.), respectively.

Synthesis of Example Compound A-5

[Chem. 19]

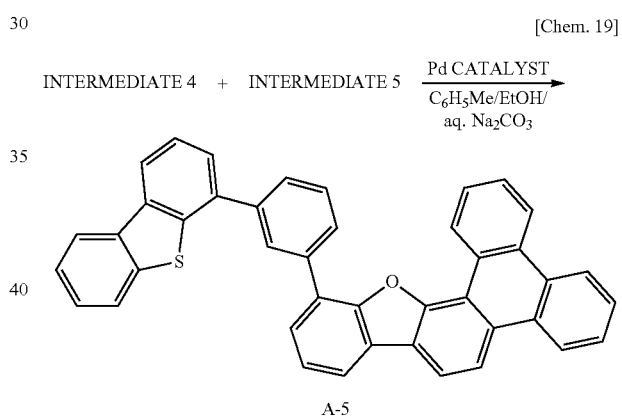

A-5

The following reagents and solvents were charged in a 30-ml eggplant flask.
Intermediate 4: 0.30 g (0.68 mmol)
Intermediate 5: 0.23 g (0.68 mmol)
Tetrakis(triphenylphosphine)palladium(0): 0.079 g (0.68 mmol)
Toluene: 4 ml
Ethanol: 0.8 ml
2M Sodium carbonate aqueous solution: 0.9 ml This reaction solution was stirred and refluxed by heating for 8 hours in a nitrogen atmosphere. After the reaction was completed, an organic layer was separated, was dried with magnesium sulfate, and was then filtered. The solvent of the filtrate thus obtained was distilled off under reduced pressure, and a viscous product was refined by a silica gel column (chloroform:heptane=1:3), so that 0.32 g of the example compound A-5 was obtained (yield: 81%). By MALDI-TOF MS, 576.2 which was M+ of this compound was confirmed.

Furthermore, the structure of this compound was confirmed by $^1$H-NMR measurement.

$^1$H-NMR (CDCl$_3$, 500 MHz) delta (ppm): 9.79 (1H, d), 8.78-8.66 (4H, m), 8.56 (1H, bs), 8.28 (1H, d), 8.23 (2H, d), 8.21 (1H, d), 8.12 (1H, d), 7.95 (1H, d), 7.85-7.80 (3H, m), 7.73 (1H, d), 7.72-7.66 (2H, m), 7.64-7.53 (3H, m), 7.51-7.44 (2H, m), 7.22 (1H, t)

In addition, Tg of the example compound A-5 measured in a manner similar to that for triphenyleno-benzofuran was 119° C.

Example 2 to 6

Synthesis of Example Compound A-2, A-3, A-4, A-10, and A-11

Each example compound was obtained by a method similar to that of Example 1 except that the intermediate 5 used for the synthesis of the example compound-A-5 of Example 1 was changed to a halogenated compound shown in Table 3.

In addition, each example compound was identified by MALDI-TOF MS.

TABLE 3

| | EXAMPLE COMPOUND | HALOGENATED COMPOUND | MALDI-TOF MS (m$^+$) |
|---|---|---|---|
| EXAMPLE 2 | A-2 | | 622.2 |
| EXAMPLE 3 | A-3 | | 586.2 |
| EXAMPLE 4 | A-4 | | 620.2 |
| EXAMPLE 5 | A-10 | | 622.3 |

TABLE 3-continued

| EXAMPLE | COMPOUND | HALOGENATED COMPOUND | MALDI-TOF MS (m+) |
|---|---|---|---|
| EXAMPLE 6 | A-11 | 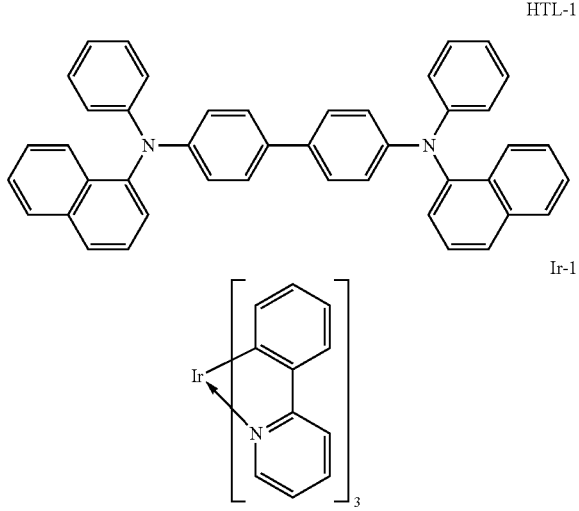 | 632.2 |

Example 7

Formation of Organic Light Emitting Element

In this example, an organic light emitting element in which an anode/hole transport layer/light emitting layer/hole blocking layer/electron transport layer/cathode were provided on a substrate in this order was formed by the following method.

An ITO film having a thickness of 120 nm was formed as an anode on the glass substrate by a sputtering method and was used as a transparent conductive support substrate (ITO substrate).

The following organic compound layers and electrode layers were sequentially formed on this ITO substrate by vacuum deposition using resistance heating in a vacuum chamber at a pressure of $10^{-5}$ Pa.

In this case, the opposing electrode was formed to have an area of 3 mm².
Hole transport layer (40 nm): HTL-1
Light emitting layer (30 nm) host material: A-5, guest material: Ir-1 (10 percent by weight)
Hole blocking (HB) layer (10 nm): HBL-1
Electron transport layer (30 nm): ETL-1
Metal electrode layer 1 (0.5 nm): LiF
Metal electrode layer 2 (100 nm): aluminum

[Chem. 20]

HTL-1

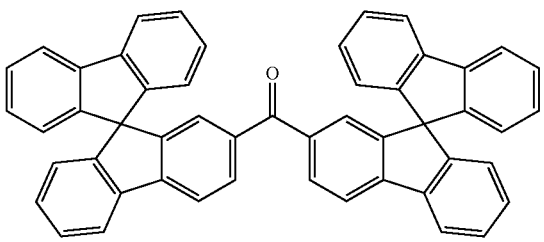

Ir-1

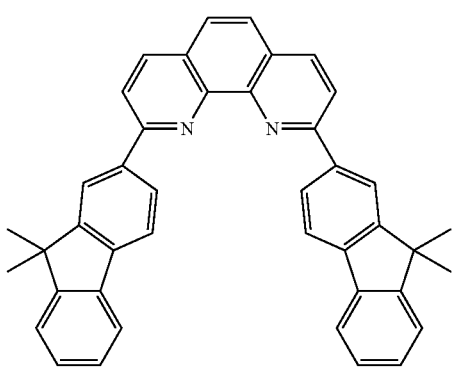

-continued

HBL-1

ETL-1

Next, in order to prevent element degradation of the organic light emitting element by absorption of water, a protective glass plate was placed in a dry air atmosphere to cover the organic light emitting element and was sealed with an acrylate resin adhesive. The organic light emitting element was obtained as described above.

The current-voltage characteristics of the organic light emitting element thus obtained were measured by an ampere meter 2700 manufactured by KEITHLEY, and the luminescent brightness was measured by BM7-fast manufactured by TOPCON CORP.

When the ITO electrode was used as a positive electrode, the Al electrode was used as a negative electrode, and a voltage of 5.3 V was applied, the green light emission having a luminance of 2,000 cd/m² was observed at a luminescent efficiency of 49 cd/A.

In addition, in this element, the CIE chromaticity coordinates were (x, y)=(0.32, 0.63).

Furthermore, the element life (time when the initial luminance was decreased by 20%) at a current density of 40 mA/cm² was 85 hours.

Examples 8 to 12

An element was formed by a method similar to that in Example 7 except that the host material used in Example 7 was changed.

In addition, when the element thus obtained was evaluated in a manner similar to that in Example 7, green light emission was observed in all Examples. The luminescent efficiency at 2,000 cd/m$^2$, the application voltage, and the element life (time when the initial luminance was decreased by 20%) at a current density of 40 mA/cm$^2$ are shown in Table 4.

TABLE 4

| EXAMPLE NO. | HOST MATERIAL | LUMINESCENT EFFICIENCY (cd/A) | VOLTAGE (V) | LIFE (h) |
| --- | --- | --- | --- | --- |
| 8 | A-2 | 53 | 5.2 | 74 |
| 9 | A-3 | 50 | 5.2 | 81 |
| 10 | A-4 | 46 | 5.0 | 89 |
| 11 | A-10 | 51 | 5.3 | 76 |
| 12 | A-11 | 53 | 5.5 | 69 |

As shown in the table, it is found that excellent luminescent efficiency and element life can be obtained when the triphenyleno-benzofuran compound of the present invention is used as the host material in the phosphorescent element.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-143203, filed Jun. 28, 2011, which is hereby incorporated by reference herein in its entirety.

The invention claimed is:

1. A triphenyleno-benzofuran compound represented by the following general formula [1]

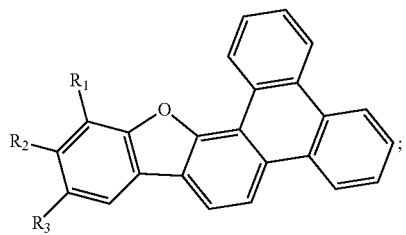

where in the general formula [1], $R_1$ to $R_3$ are each independently selected from the group consisting of a hydrogen atom and a substituted or unsubstituted aryl group, at least one of $R_1$ to $R_3$ represents the aryl group, and the aryl group represents a group selected from the group consisting of a substituted or unsubstituted fluorenyl group which bound to the triphenyleno-benzofuran backbone at 2 to 4 positon of the fluorenyl group, and a substituted or unsubstituted chrysenyl group, and wherein each of the fluorenyl group and the chrysenyl group represented by the aryl group may have a substituent selected from the group consisting of an alkyl group, a phenyl group, a biphenyl group, a terphenyl group, a naphthyl group, a phenanthrenyl group, a fluorenyl group, a chrysenyl group, and a dibenzothienyl group, and wherein the phenyl group, the biphenyl group, the terphenyl group, the naphthyl group, the phenanthrenyl group, the fluorenyl group, the chrysenyl group, and the dibenzothienyl group as a substituent of the fluorenyl group and the chrysenyl group are optionally substituted by an alkyl group.

2. The triphenyleno-benzofuran compound according to claim 1, wherein in the general formula [1], $R_1$ represents the aryl group, and $R_2$ and $R_3$ each represent a hydrogen atom.

3. An organic light emitting element comprising:

an anode, a cathode, and at least one organic compound layer arranged between the anode and the cathode, wherein the organic compound layer includes the triphenyleno-benzofuran compound according to claim 1.

4. The organic light emitting element according to claim 3, wherein the at least one organic compound layer includes a light emitting layer, and the light emitting layer includes the triphenyleno-benzofuran compound.

5. The organic light emitting element according to claim 4, wherein the light emitting layer has a host material and a guest material, the host material includes the triphenyleno-benzofuran compound, and the guest material is a phosphorescent material.

6. The organic light emitting element according to claim 5, wherein the phosphorescent material includes an iridium complex.

7. A display device comprising:

a plurality of pixels, wherein the pixels each include the organic light emitting element according to claim 3 and a switching element connected thereto.

8. An image input device comprising:

a display portion to display an image; and an input portion to input image information, wherein the display portion includes a plurality of pixels, and the pixels each include the organic light emitting element according to claim 3 and a switching element connected thereto.

9. A lighting device comprising:

the organic light emitting element according to claim 3; and an inverter circuit connected thereto.

10. A display device comprising:

a plurality of pixels, wherein the pixels each include the organic light emitting element according to claim 4 and a switching element connected thereto.

11. An image input device comprising:

a display portion to display an image; and an input portion to input image information, wherein the display portion includes a plurality of pixels, and the pixels each include the organic light emitting element according to claim 4 and a switching element connected thereto.

12. A lighting device comprising:
the organic light emitting element according to claim 4; and
an inverter circuit connected thereto.

13. A display device comprising:
a plurality of pixels,
wherein the plurality of pixels each include the organic light emitting element according to claim 5 and a switching element connected thereto.

14. A lighting device comprising:
the organic light emitting element according to claim 5; and
an inverter circuit connected thereto.

15. A display device comprising:
a plurality of pixels,
wherein the plurality of pixels each include the organic light emitting element according to claim 6 and a switching element connected thereto.

16. An image input device comprising:
a display portion to display an image; and
an input portion to input image information,
wherein the display portion includes a plurality of pixels, and
the plurality of pixels each include the organic light emitting element according to claim 6 and a switching element connected thereto.

17. A lighting device comprising:
the organic light emitting element according to claim 6; and
an inverter circuit connected thereto.

18. The triphenyleno-benzofuran compound according to claim 1, wherein the triphenyleno-benzofuran compound has an SP3 carbon atom.

19. The triphenyleno-benzofuran compound according to claim 18, wherein the SP3 carbon atom is included in an alkyl group.

20. A triphenyleno-benzofuran compound represented by any one of the following structures:

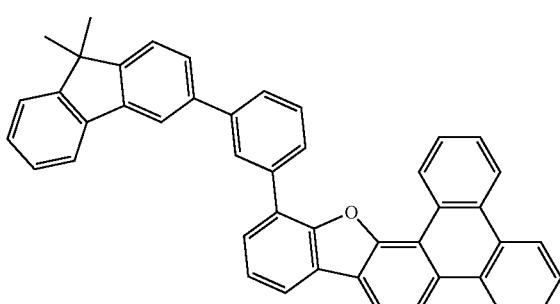

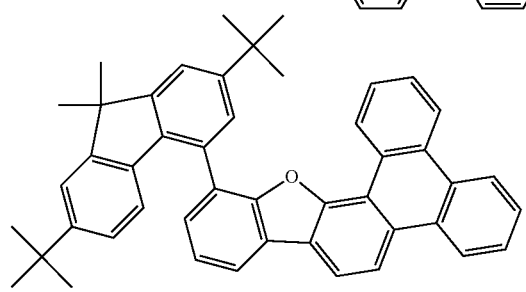

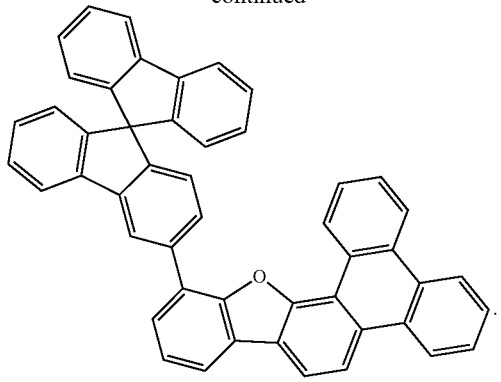

21. A triphenyleno-benzofuran compound represented by the following general formula [1]

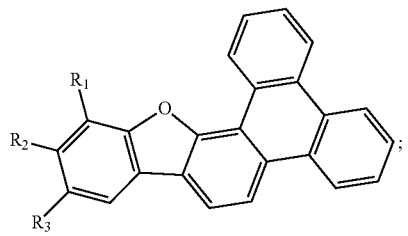

[1]

where in the general formula [1], $R_1$ to $R_3$ are each independently selected from the group consisting of a hydrogen atom and a substituted or unsubstituted aryl group,
at least one of $R_1$ to $R_3$ represents the aryl group, and
the aryl group represents a group selected from the group consisting of a substituted or unsubstituted phenyl group, and a substituted or unsubstituted chrysenyl group,
wherein the phenyl group represented by the aryl group may have a substituent selected from the group consisting of a naphthyl group, a phenanthrenyl group, a fluorenyl group, a chrysenyl group, and a dibenzothienyl group,
wherein the chrysenyl group represented by the aryl group may have a substituent selected from the group consisting of an alkyl group, a phenyl group, a biphenyl group, a terphenyl group, a naphthyl group, a phenanthrenyl group, a fluorenyl group, a chrysenyl group, and a dibenzothienyl group,
wherein the phenyl group, the biphenyl group, the terphenyl group, the naphthyl group, the phenanthrenyl group, the fluorenyl group, the chrysenyl group, and the dibenzothienyl group as a substituent of the chrysenyl group are optionally substituted by an alkyl group, and
wherein the naphthyl group, the phenanthrenyl group, the fluorenyl group, the chrysenyl group, and the dibenzothienyl group as a substituent of the substituted phenyl group are optionally substituted by an alkyl group.

* * * * *